(12) United States Patent
Bales, Jr. et al.

(10) Patent No.: US 6,313,409 B1
(45) Date of Patent: *Nov. 6, 2001

(54) ELECTRICAL CONDUCTORS AND METHODS OF MAKING SAME

(75) Inventors: Thomas O. Bales, Jr.; Francisco Avellanet, both of Coral Gables, FL (US)

(73) Assignee: General Science and Technology Corp, Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/048,746

(22) Filed: Mar. 26, 1998

Related U.S. Application Data (63) Continuation-in-part of application No. 08/843,405, filed on May 2, 1997, now Pat. No. 5,994,647, and a continuation-in-part of application No. 08/963,686, filed on Nov. 4, 1997, now Pat. No. 6,049,042.

(51) Int. Cl.$^7$ ........................................ H01B 5/10

(52) U.S. Cl. ........................................ 174/128.1

(58) Field of Search ..................... 174/126.1, 126.2, 174/128.1, 128.2, 129 R, 133 R, 125.1

(56) References Cited

U.S. PATENT DOCUMENTS

| | | | |
|---|---|---|---|
| H1239 | 10/1993 | Dusek | ........................... 264/63 |
| 251,114 | 12/1881 | Hallidie . | |

(List continued on next page.)

FOREIGN PATENT DOCUMENTS

| | | |
|---|---|---|
| 595245 | 4/1934 | (DE) . |
| 0480427A1 | 10/1991 | (EP) . |

(List continued on next page.)

OTHER PUBLICATIONS

Suhner, How to produce efficiently flexible shafts and casings; May/Jun. 1978, Wire, pp 109–112.

W.Berg, More twists for flexible shafts couplings; Aug. 21, 1997, Machine Design, p. 152.

(List continued on next page.)

*Primary Examiner*—Chau N. Nguyen
(74) *Attorney, Agent, or Firm*—David P Gordon; David S. Jacobson; Thomas A Gallagher (57) ABSTRACT

Electrical conductors according to the invention include conductors made from a plurality of strands twisted around a central conductor, where the strands are fused to the central conductor but not to each other. According to a preferred embodiment, the central conductor is coated with a coating of a first material which may be melted to fuse the central conductor to the outer strands. In another preferred embodiment, the outer strands are also coated with a second conductive material which forms a eutectic mixture with the coating on the central conductor when heated to a temperature below the melting points of the first and second conductive materials. Alternate embodiments of the invention provide a eutectic mixture by choice of strand and central conductor material and/or coating. If desired, the conductor is deformed prior to melting the coating(s) such as by drawing or swaging to form a conductor with a substantially circular cross section or by rolling or drawing to form a conductor with a substantially rectangular cross section. In still another embodiment, the conductor is formed as a coil prior to melting the coating(s). The conductors of the invention exhibit enhanced electrical and physical characteristics and are particularly well suited for use in conducting VHF and UHF signals and for making coils.

14 Claims, 4 Drawing Sheets

U.S. PATENT DOCUMENTS

| | | | |
|---|---|---|---|
| 1,691,869 * | 11/1928 | Fowle | 174/128.1 |
| 1,738,828 * | 12/1929 | Jackson | 174/126.2 |
| 1,742,172 | 12/1929 | Atwood . | |
| 1,888,076 | 11/1932 | Evans . | |
| 1,888,807 | 11/1932 | Rivers . | |
| 1,904,162 | 4/1933 | Milliken . | |
| 1,943,082 | 1/1934 | MacKenzie | 261/49 |
| 1,943,086 | 1/1934 | McKnight | 173/264 |
| 1,943,087 | 1/1934 | Potter | 173/264 |
| 2,071,709 | 2/1937 | Riddle | 117/16 |
| 2,135,800 | 11/1938 | Davignon | 88/52 |
| 2,154,551 | 4/1939 | Wodtke | 174/128 |
| 2,156,652 | 5/1939 | Harris | 57/145 |
| 2,396,734 | 3/1946 | Williams, Jr. | 174/128 |
| 2,427,507 | 9/1947 | Powell, 3rd | 57/164 |
| 2,978,860 | 4/1961 | Campbell | 57/148 |
| 3,006,384 | 10/1961 | Brown et al. | 139/425 |
| 3,083,817 | 4/1963 | Campbell | 205/2 |
| 3,130,536 | 4/1964 | Peterson et al. | 57/161 |
| 3,131,469 | 5/1964 | Glaze | 29/470.5 |
| 3,195,299 | 7/1965 | Dietz | 57/149 |
| 3,234,722 | 2/1966 | Gilmore | 57/145 |
| 3,261,908 | 7/1966 | Roche et al. | 174/128 |
| 3,295,310 | 1/1967 | Beighley | 57/145 |
| 3,333,045 | 7/1967 | Fisher et al. | 174/20 |
| 3,352,098 | 11/1967 | Gilmore | 57/147 |
| 3,383,704 | 5/1968 | Schoerner et al. | 57/145 |
| 3,395,528 | 8/1968 | Lucht et al. | 57/145 |
| 3,444,684 | 5/1969 | Schoerner et al. | 57/161 |
| 3,601,970 | 8/1971 | Roberts et al. | 57/153 |
| 3,699,768 | 10/1972 | Roberts et al. | 57/144 |
| 3,812,666 | 5/1974 | Sarracino | 57/58.52 |
| 3,822,542 | 7/1974 | Naud et al. | 57/145 |
| 3,831,370 | 8/1974 | Gilmore | 57/145 |
| 3,842,185 | 10/1974 | Raw et al. | 174/23 R |
| 3,883,278 | 5/1975 | Hass | 425/135 |
| 3,883,371 | 5/1975 | Geary | 148/32 |
| 3,900,347 | 8/1975 | Lorenzetti et al. | 148/12 B |
| 3,922,841 | 12/1975 | Katsumata et al. | 57/145 |
| 3,923,003 | 12/1975 | Carden | 118/405 |
| 3,934,446 | 1/1976 | Avitzur | 72/206 |
| 3,942,309 | 3/1976 | Cahill | 57/9 |
| 3,955,390 | 5/1976 | Geary | 72/64 |
| 3,961,514 | 6/1976 | Geary | 72/274 |
| 3,972,304 | 8/1976 | Boucher | 118/44 |
| 3,990,874 | 11/1976 | Schulman | 65/4 B |
| 4,020,829 | 5/1977 | Willson | 128/2 M |
| 4,079,510 | 3/1978 | McGrath et al. | 29/624 |
| 4,125,741 | 11/1978 | Wahl et al. | 174/120 |
| 4,133,167 | 1/1979 | Schofield | 57/12 |
| 4,173,235 | 11/1979 | Tipper | 140/82 |
| 4,201,250 | 5/1980 | Walling et al. | 141/250 |
| 4,212,151 | 7/1980 | Schauffele et al. | 57/9 |
| 4,215,703 | 8/1980 | Willson | 128/772 |
| 4,311,001 | 1/1982 | Glushko et al. | 57/215 |
| 4,328,662 | 5/1982 | Bretegnier et al. | 57/58.61 |
| 4,330,956 | 5/1982 | McCarthy | 43/4 |
| 4,349,694 | 9/1982 | Vives | 174/128 R |
| 4,352,697 | 10/1982 | Adams et al. | 148/2 |
| 4,354,880 | 10/1982 | Adams et al. | 148/2 |
| 4,406,058 | 9/1983 | Dixon | 29/809 |
| 4,456,491 | 6/1984 | Adams et al. | 148/2 |
| 4,471,527 | 9/1984 | Nishijima | 29/872 |
| 4,473,995 | 10/1984 | Gentry | 57/9 |
| 4,497,867 * | 2/1985 | Bely et al. | 174/126.2 X |
| 4,514,058 | 4/1985 | Walton | 350/96.23 |
| 4,525,598 | 6/1985 | Tsukamoto et al. | 174/128 |
| 4,529,837 | 7/1985 | Borden | 174/128 |
| 4,534,363 | 8/1985 | Gold | 128/772 |
| 4,548,206 | 10/1985 | Osborne | 128/772 |
| 4,579,127 | 4/1986 | Haacke | 128/772 |
| 4,634,042 | 1/1987 | Smith | 228/173.4 |
| 4,651,513 | 3/1987 | Dambre | 57/217 |
| 4,654,477 | 3/1987 | Isoda | 174/128 R |
| 4,679,387 | 7/1987 | Weidenhaupt et al. | 57/212 |
| 4,682,607 | 7/1987 | Vaillancourt | 128/772 |
| 4,689,444 | 8/1987 | Burgess | 174/128 R |
| 4,705,096 | 11/1987 | Chia | 164/476 |
| 4,731,134 | 3/1988 | Alloin et al. | 156/53 |
| 4,759,806 | 7/1988 | Dambre | 148/12 B |
| 4,763,466 | 8/1988 | Abe et al. | 57/213 |
| 4,777,324 | 10/1988 | Lee | 174/34 |
| 4,778,246 | 10/1988 | Carroll | 350/96.23 |
| 4,843,696 | 7/1989 | Gentry et al. | 29/33 F |
| 4,922,924 | 5/1990 | Gambale | 128/772 |
| 4,925,445 | 5/1990 | Sakamoto et al. | 604/95 |
| 5,018,993 | 5/1991 | Durham | 439/801 |
| 5,069,217 | 12/1991 | Flesichhacker | 128/657 |
| 5,074,140 | 12/1991 | Sanders | 72/248 |
| 5,129,890 | 7/1992 | Bates et al. | 604/281 |
| 5,133,121 | 7/1992 | Birbeck et al. | 29/872 |
| 5,147,662 | 9/1992 | Nishijima et al. | 425/500 |
| 5,167,399 | 12/1992 | Delomel | 254/134.3 R |
| 5,190,546 | 3/1993 | Jervis | 606/78 |
| 5,211,772 | 5/1993 | Ashida et al. | 148/336 |
| 5,213,111 | 5/1993 | Cook et al. | 128/772 |
| 5,215,246 | 6/1993 | Thompson et al. | 228/171 |
| 5,217,026 | 6/1993 | Stoy et al. | 128/772 |
| 5,230,348 | 7/1993 | Ishibe et al. | 128/772 |
| 5,240,520 | 8/1993 | Tarui et al. | 148/532 |
| 5,242,759 | 9/1993 | Hall | 428/610 |
| 5,251,640 | 10/1993 | Osborne | 128/772 |
| 5,260,516 | 11/1993 | Blackmore | 174/113 A |
| 5,286,577 | 2/1994 | Premkumar et al. | 428/558 |
| 5,322,508 | 6/1994 | Viera | 604/52 |
| 5,333,620 | 8/1994 | Moutafis et al. | 128/772 |
| 5,334,166 | 8/1994 | Palestrant | 604/265 |
| 5,343,934 | 9/1994 | Wilson | 428/610 |
| 5,368,661 | 11/1994 | Nakamura et al. | 148/512 |
| 5,417,690 | 5/1995 | Sennett | 606/61 |
| 5,418,333 | 5/1995 | Sanders | 174/129 |
| 5,429,139 | 7/1995 | Sauter | 128/772 |
| 5,433,200 | 7/1995 | Flesichhacker | 128/657 |
| 5,437,288 | 8/1995 | Schwartz et al. | 128/772 |
| 5,437,748 | 8/1995 | Bhagwat et al. | 148/532 |
| 5,439,000 | 8/1995 | Gunderson | 128/664 |
| 5,451,718 | 9/1995 | Dixon | 174/102 R |
| 5,486,183 | 1/1996 | Middleman et al. | 606/127 |
| 5,520,194 | 5/1996 | Miyata et al. | 128/772 |
| 5,535,612 | 7/1996 | Vijayakar | 72/43 |
| 5,571,086 | 11/1996 | Kaplan et al. | 604/96 |
| 5,571,087 | 11/1996 | Ressemann | 604/96 |
| 5,571,094 | 11/1996 | Sirhan | 604/284 |
| 5,588,443 | 12/1996 | Davidson | 128/772 |
| 5,597,378 | 1/1997 | Jervis | 606/78 |
| 5,616,197 | 4/1997 | Helfer et al. | 152/527 |
| 5,632,746 | 5/1997 | Middleman et al. | 606/78 |
| 5,709,760 | 1/1998 | Prakash | 152/556 |
| 5,732,875 * | 3/1998 | Ziemek et al. | 174/129 R X |

FOREIGN PATENT DOCUMENTS

| | | |
|---|---|---|
| 0 537 618A1 | 4/1993 | (EP) . |
| 0666086A1 | 2/1994 | (EP) . |
| 0642 876 A1 | 8/1994 | (EP) . |
| 0649636A2 | 9/1994 | (EP) . |
| 0649636A3 | 9/1994 | (EP) . |
| 278233 | 10/1927 | (GB) . |

OTHER PUBLICATIONS

Fogiel, Modern Microelectronics, 1972, pp 735–737.

Kelly, A Plating Process for Ensuring Component Lead Solderability, SMT, Oct. 1997, pp 68,70.

Hesterlee, Trapwire Constructions; Wire Technology/International, Mar. 1997, pp 51–53.

Wright, A Short Discussion of the significance of the Delta Parameter in wire drawing, Wire Journal, Oct. 1979, pp 60–61.

Reducing Restenosis with Endovascular Brachytherapy, Medpro Month, Jan. 1998, vol. VIII, No. 1.

* cited by examiner

ELECTRICAL CONDUCTORS AND METHODS OF MAKING SAME

This application is a continuation-in-part of application Ser. No. 08/843,405 filed May 2, 1997 now U.S. Pat. No. 5,994,647 and a continuation-in-part of Ser. No. 08/963,686 filed Nov. 4, 1997 now U.S. Pat. No. 6,049,042, the complete disclosures of which are hereby incorporated by reference herein.

BACKGROUND OF THE INVENTION

1. Field of the Invention

The invention relates to electrical conductors. More particularly, the invention relates to electrical conductors which exhibit low resistance, spatial efficiency, low weight, good flexibility, enhanced bandwidth, minimized parasitic capacitance and inductance, and which are well suited for use, for example, in VHF and UHF transmission lines as well as in coils, solenoids, motors, and transformers.

2. State of the Art

Parent application Ser. No. 08/843,405 which is referenced above describes the general techniques known in the art for making electrical cables from helically twisted filaments, and proposes methods of twisting and drawing wire cables for enhancing the conductivity, flexibility and tensile strength of the cables. In addition to low resistance, flexibility and tensile strength, other characteristics of cables may be important depending on the application in which the cable is used. For example, the ability of a cable to remain cool during operation is often an important consideration. For cables used outdoors for power transmission, renitence to corrosion and low weight of the cable are important considerations. For cables which are subjected to repeated flexion, good flexibility as well as high fatigue strength are important. In cables which are used as leads for semiconductors and other electronic components, parasitic capacitance and inductance are important considerations.

Parent application Ser. No. 08/963,686 which is referenced above discloses cables made from plated filaments which are first twisted together and then drawn through reducing dies (or swaged), filaments which are twisted together around a core material which melts or deforms during drawing of the cable through reducing dies, filaments which are twisted around a tube prior to drawing through reducing dies, and cables which are made from combinations of these methods. The cables exhibit a conductivity comparable to cables having greater diameter and weight. The smaller diameter of the cables of the invention allows them to be used as leads for electronic components in order to achieve reduced parasitic capacitance without increased resistivity or reactance or component package size. The cold working of the cables of the invention provides them with enhanced flexibility and fatigue strength. The combination of materials used in the cables of the invention provides them with renitence to corrosion and the adverse affects of aging as well as enhanced conductivity. Cables formed with a hollow tube core can be self-cooling, or easily cooled by flowing a coolant through the hollow core. The hollow tube core also enhances fatigue strength, resists the effects of aging, and lowers the weight of the cable. Cables formed with a silver core are also self-cooling.

Both of the parent applications recognize that multi-stranded electrical cable is generally more flexible than a single strand conductor which has similar conductive capacity. It is also recognized in the parent applications that multi-stranded cables have several disadvantages compared to single strand conductors. In particular, the parent applications teach that multi-stranded cables are spatially inefficient and possess self-induced parasitic inductance because of the helical paths of the strands which are not in perfect contact with each other. It is also recognized that the helical paths of the strands results in a longer conductive path (known as the "lay effect") and a corresponding increase in resistivity.

The physical properties of multi-stranded electrical cable also cause poor performance at very high frequencies (VHF) and ultra high frequencies (UHF). Signal losses at these frequencies are the result of multiple signal reflections along the length of a multi-stranded transmission line. Reflections occur where the cable exhibits an abrupt change in impedance due to the imperfect contact of the strands with each other. The reflected signals are typically out of phase with the transmitted signal and interfere destructively with the transmitted signal. This results in a "smearing" of signal pulses which limits the bandwidth of the transmission line.

The twisted and drawn multi-stranded wires of the parent applications maximize the spatial efficiency of a generally cylindrical conductor and achieve many other advantages as described above. However, there are certain applications where a generally cylindrical conductor is not the most spatially efficient. For example, where a conductor is wound to form a coil, a cylindrical cross-section is not necessarily the most spatially efficient.

The twisted and drawn multi-stranded wires of the parent applications also generally possess enhanced flexibility. However, certain electrical coils require relatively large diameter conductors wound to a relatively small radius. Winding a large diameter conductor to form a small diameter coil is difficult because the large diameter conductor may not have the flexibility to be wound so tightly. Use of a multi-strand conductor for such a coil introduces other problems regarding conductivity as described above. Moreover, it is usually desirable that the finished coil be inflexible. In addition, when a multi-strand conductor is formed into a non-circular cross section, individual strands are pinched irregularly such that their cross sections change along their length. This change in cross sectional shape (even if cross sectional area remains the same) increases the resistivity of the conductor (known as the "pinch effect").

SUMMARY OF THE INVENTION

It is therefore an object of the invention to provide an electrical conductor which has low electrical resistance and which exhibits reduced parasitic capacitance and inductance.

It is also an object of the invention to provide an electrical conductor which has a structure which is spatially efficient.

It is another object of the invention to provide an electrical conductor which has a high bandwidth when used as a signal transmission line.

It is a further object of the invention to provide an electrical conductor which is well suited for use in coils, solenoids, motors, and transformers.

Another object of the invention is to provide methods of making electrical conductors and coils.

In accord with these objects which will be discussed in detail below, the electrical conductors of the present invention are made by winding several strands around a center strand and fusing the outer strands to the center strand, but not to each other. Preferably, at least the center strand is coated with a first material, wherein the coating may be melted to fuse the outer strands to the center. If desired, the outer strands may be coated with a second material which will form a eutectic melting mixture with the first material. According to a preferred embodiment, the coated strands are first twisted together and then drawn through reducing dies (or swaged) prior to brazing. The conductor may be further drawn or swaged while being subjected to brazing heat. Brazing may be enhanced through the use of reforming gas of soldering flux. The conductor thus formed has continuous, metallurgical bonding among the strands such that each outer strand is directly and continuously connected to the center strand, reducing the effects of helical conduction, but the outer strands are not bonded to each other, thereby maintaining the flexibility of stranded wire. Also, since the outer strands do not constitute separate helical conductors, the inductive effect and the associated inductive reactance, are reduced. Most importantly, the finished conductor will have much more stable performance characteristics, and the effects of multiple resistive contacts among the strands will be ameliorated, since each outer strand is solidly connected to the center strand throughout its length, allowing the conductor to be a much better conductor of signals in the VHF and UHF ranges.

According to alternate embodiments, different arrangements for generating fusing via eutectic mixtures are employed. In one alternate embodiment, the center and outer strands are not coated but are made of respective materials which form a eutectic mixture when appropriately heated. In another alternate embodiment the center strand is coated with a first material and the outer strands are formed from another material which forms a eutectic mixture with the coating of the center strand when appropriately heated. In yet another alternative embodiment, the center strand is uncoated and formed of a first material, while one or more of the outer strands are coated with a second material which forms a eutectic mixture with the center strand when appropriately heated.

According to another aspect of the invention, a multifilament twisted and drawn conductor is further shaped to provide the conductor with a non-circular cross section. According to a presently preferred embodiment, the conductor is rolled or drawn through dies to provide it with a preferably rectangular or otherwise polygonal cross section. The change in cross section shape is effected through successive steps to avoid pinching and the cross sectional area of the conductor may be further reduced without changing its cross section. It is preferred, however, that the cross section of the conductor be acted upon in all directions simultaneously so that the individual strands do not separate. According to a preferred embodiment, the stranded conductor is brazed as described above prior to shaping its cross section. These shaped conductors are particularly well suited for use in coils, solenoids, motors, and transformers where they exhibit extraordinary spatial efficiency.

As mentioned above, certain relatively small diameter coils made of relatively large diameter conductors are difficult to make because of pinching. According to another aspect of the invention, a stranded conductor coated with a meltable material is formed into a coil prior to brazing as described above.

A conductor combining all of the aspects of the invention includes a multi-stranded conductor where the strands are coated with different conductive coatings to form a eutectic mixture, the strands being twisted and drawn and shaped to have a rectangular cross section. The conductor is then wound to form a coil and heated to the eutectic melting point such that the strands are brazed and the cooled coil exhibits a desirable rigidity.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
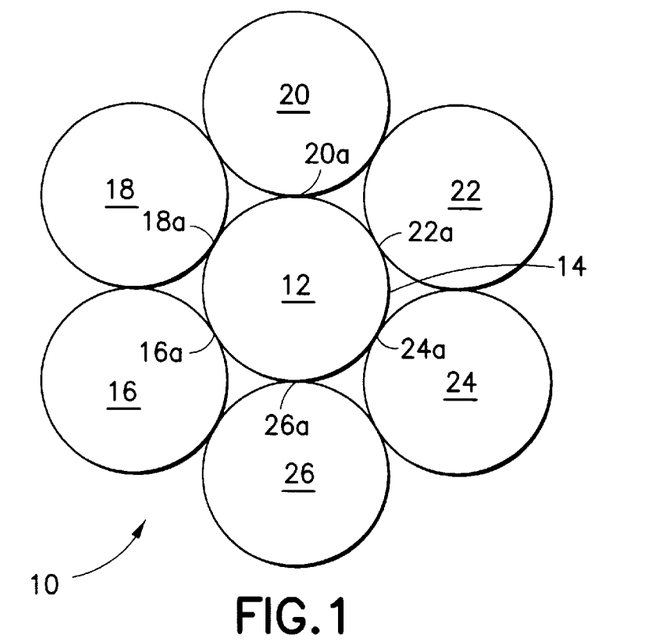
FIG. 1 is a schematic sectional view of a first embodiment of an electrical conductor according to the invention.

Turning now to FIG. 1, an electrical conductor 10 according to a first embodiment of the invention includes a center strand 12 (e.g. 0.010 inch diameter copper) which is coated with a conductive material 14, such as tin plating (e.g. 300 microinches thick). Six outer strands copper strands 16, 18, 20, 22, 24, 26 are twisted around the center strand 12. The seven strands, so assembled are heated to a temperature sufficient to melt the coating of the center strand (but below the melting temperature of the seven strands) and then cooled to normal ambient temperature. The result of melting and then solidifying the conductive coating on the center strand 12 is the formation of bonds 16a, 18a, 20a, 22a, 24a, 26a between the center strand 12 and each of the outer strands 16, 18, 20, 22, 24, 26 along the line at which the strands contact each other. This electrical bonding improves the electrical performance of the conductor as described above. However, there is no bonding between adjacent outer strands because there is insufficient meltable conductive material to wick outward from the center strand and bond the outer strands to one another. Thus, the mechanical performance of the multistranded conductor is maintained.

Figure 2:
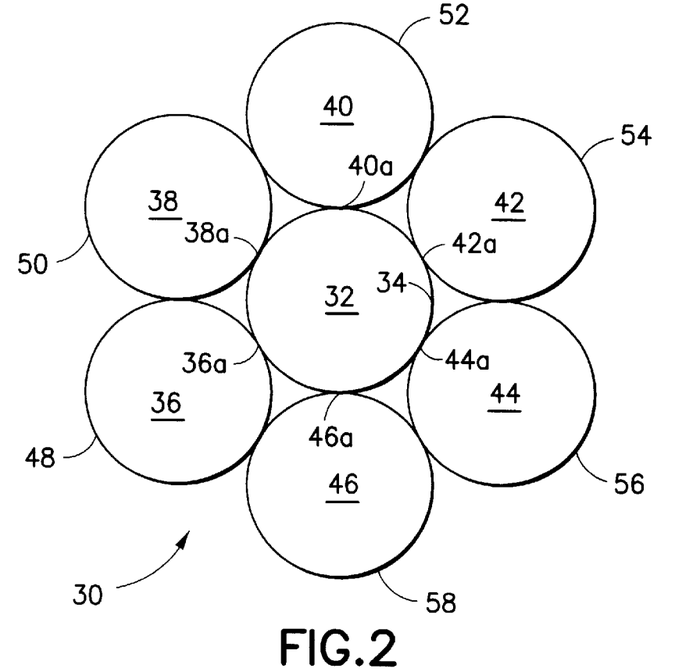
FIG. 2 is a view similar to FIG. 1 of a second embodiment of an electrical conductor according to the invention.

Turning now to FIG. 2, a conductor 30, according to a second embodiment of the invention includes a center copper 0.010 inch diameter strand 32 which is provided with a lead coating 34 approximately 300 microinches thick. At least some, and preferably all, of six 0.010 inch diameter outer strands 36, 38, 40, 42, 44, 46 are provided with a tin coating 48, 50, 52, 54, 56, 58 approximately 300 microinches thick. The six outer strands are twisted about the center strand and the assembly is heated as described below and cooled. According to this embodiment, the coatings for the center strand 32 and the outer strands 36, 38, 40, 42, 44, 46 are chosen to be components of a eutectic melting mixture. Thus, according to this example, lead has a melting point of 621° F., tin has a melting point of 449° F., and a eutectic 63:37 tin:lead mixture has a melting point of 361°

F. According to this embodiment of the invention, the assembled strands are heated to a temperature above the eutectic melting point but below the melting point of the individual coatings on the strands. Thus, according to this example, the assembled strands are heated to approximately 400° F. and then cooled to ambient temperature. This heating results in a bonding of the outer strands 36, 38, 40, 42, 44, 46 to the center strand 32 along contact lines 36a, 38a, 40a, 42a, 44a, 46a. However, the use of a eutectic melting mixture prevents the outer strands 36, 38, 40, 42, 44, 46 from bonding to each other.

Another example of this embodiment is where the center conductor is coated with silver and the outer conductors are coated with tin. As mentioned above, tin melts at 449° F. Silver melts at 1761° F. and the eutectic mixture of 2.7% silver and 97.5% tin melts at 430° F. Thus, according to this embodiment, the stranded conductor assembly is processed at a temperature above 430° F. but below 449° F.

Figure 8:
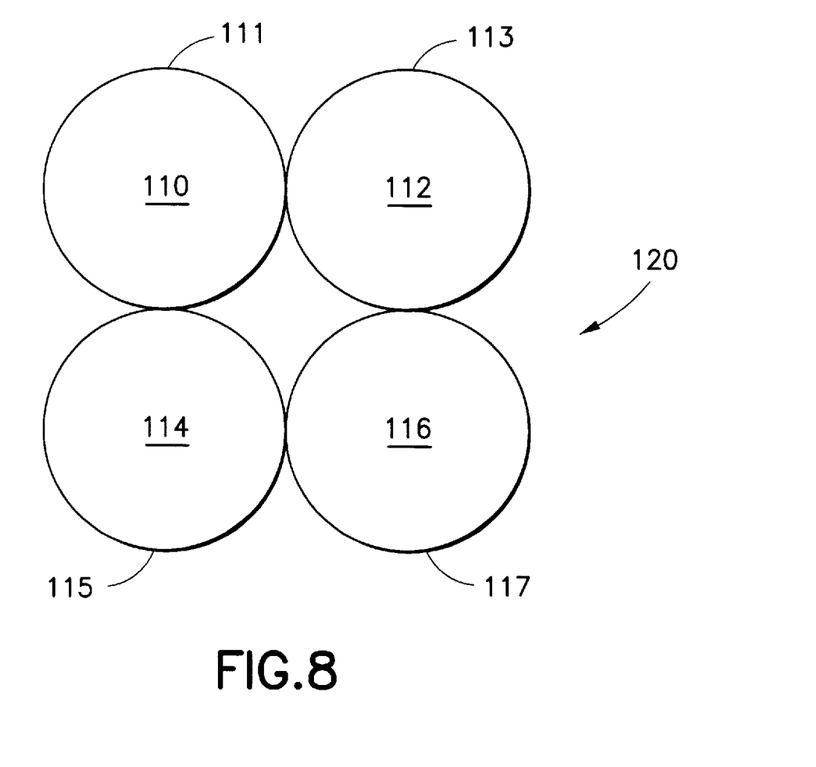
FIG. 8 is a schematic illustration of fourth embodiment of an electrical conductor according to the invention.
Figure 9:
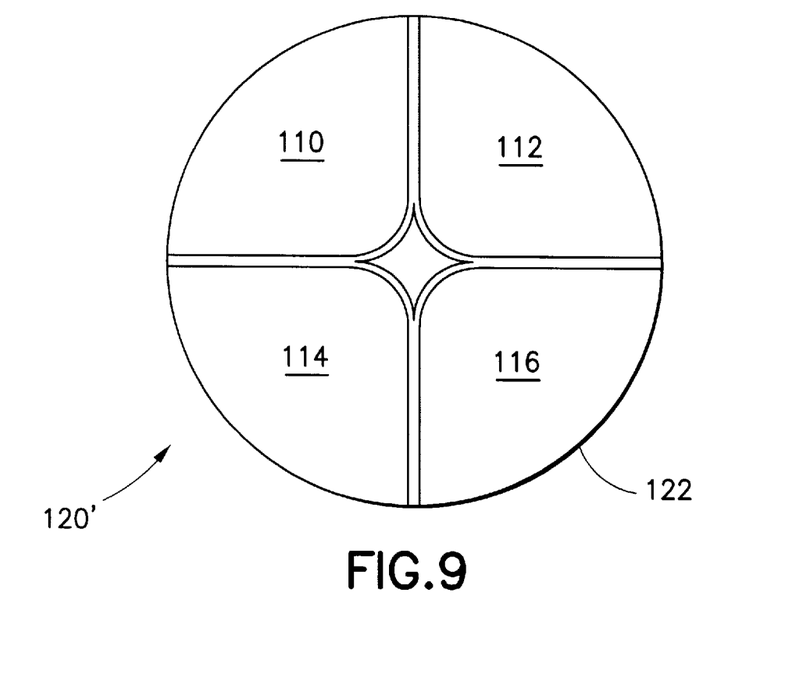
FIG. 9 is a schematic illustration of fifth embodiment of an electrical conductor according to the invention.

According to alternate embodiments, different arrangements for generating eutectic mixtures are employed. In one alternate embodiment, as shown in FIG. 8 the center and outer strands 54, 56, 58, 60, 62, 64 are not coated but are made of respective materials which form a eutectic mixture when appropriately heated. In another alternate embodiment the center strand is coated with a first material and the outer strands are formed from another material which forms a eutectic mixture with the coating of the center strand when appropriately heated. In yet another alternative embodiment, as shown in FIG. 9 the center strand 72 is uncoated and formed of a first material, while one or more of the outer strands 74, 76, 78, 80, 82, 84 are coated with a second material which forms a eutectic mixture with the center strand when appropriately heated.

According to an alternate embodiment of the invention, the stranded conductor is subjected to a mechanical deformation to compress the assembly after stranding but before brazing. For example, the conductor 30 described above is drawn through one or more dies as described in the parent applications whereby it assumes a compressed configuration 30' similar to that shown in FIG. 3. According to the invention, the drawing of the wire is preferably accomplished without the use of a lubricant which might interfere with the subsequent brazing step. The drawing process reduces the overall diameter of the stranded assembly and also makes the assembly assume a substantially round cross section. The interstitial air spaces between the strands are substantially eliminated and the strands are brought into intimate contact with each other. For example, the 1×7 stranded conductor described above as being made of seven 0.010 inch diameter strands has an overall diameter of approximately 0.030 inches. This overall diameter can be reduced by drawing to approximately 0.014 inches, resulting in substantial compaction of the strands.

Figure 3:
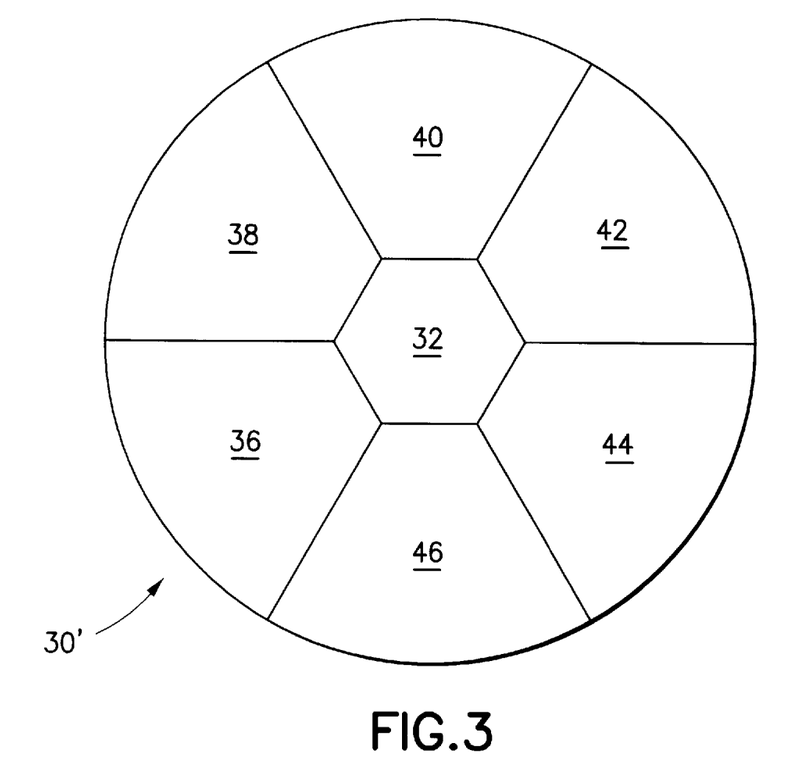
FIG. 3 is a view similar to FIGS. 1 and 2 of a third embodiment of an electrical conductor according to the invention.

As shown in FIG. 3, compaction forces the center strand 32 into an hexagonal shape, and the outer strands 36, 38, 40, 42, 44, 46 are forced into contact with each other with their surfaces meeting along a substantially radial plane. Once this compaction has been accomplished (or during compaction), the assembly of strands is subjected to the bonding temperature as described above which results in fully bonding the center strand 32 to each of the outer strands 36, 38, 40, 42, 44, 46, but does not bond the outer strands to one another. This construction also results in a highly efficient use of space in the conductor 30', since there are substantially no air spaces in the conductor. Moreover, the flexibility of the conductor is enhanced because the overall radius of the conductor is reduced. This results in a lower polar moment of the conductor, which reduces the bending stiffness of the conductor. In fact, the stiffness of the conductor is the minimum possible for any conductor containing the same cross-sectional area and having the same number of strands.

In all of the embodiments, the bonding process may be carried out in several ways. If the conductor is still in linear form (i.e., not wound into a coil or onto a spool), additional contact pressure can be applied by passing the conductor between rolls or through a die at the desired temperature to assure contact mixing and full bonding. If the conductor is covered by a deformable insulation (such as PTFE or polyamide) which will not melt at the desired bonding temperature, the bonding may be done after the insulation is applied. In this case additional contact pressure to improve bonding may be applied by subjecting the insulated wire to hydrostatic pressure by means of an autoclave. Autoclave pressure may be applied to the wire in a continuous in-line process, where the wire is passed into and out of a heated pressure chamber through seals. Alternatively, autoclaving may be done by placing spools of insulated wire into a heated pressure chamber. Moreover, as described below with reference to FIGS. 4 and 7, the wire may be wound or formed into coils or other forms, and then the finished coils placed into the autoclave chamber for heat and pressure processing to achieve eutectic bonding.

In order to ensure the wetting of the inner strand to the outer strands, it may be advantageous to perform the baking operation in a reducing atmosphere (e.g., in the presence of dry hydrogen gas or "reforming gas" which is nitrogen plus hydrogen), in order to remove any oxides which may be present on the conductor strands. Alternatively, the strands may be coated with a thin coating of a non-activated or mildly-activated soldering flux, which does not require removal after fusing of the outer strands to the inner strand.

Each of the embodiments described thus far possesses a conductor structure, which has continuous, metallurgical bonding such that each outer strand is directly and continuously connected to the center strand. The result of this connection is to reduce certain undesired electrical effects of helical stranding while keeping the positive physical attributes. In particular, the center strand is a shorter and straighter path for current flow and hence a path of lower resistance. Bonding the outer strands to the center strand effectively shunts the helical outer conductor strands causing some proportion of the current in the outer strands to be carried by the center strand. Also, since the outer strands no longer constitute separate helical conductors, the inductive effect and the associated inductance/reactance are reduced. Most importantly, the finished conductor has much more stable performance characteristics, and the effects of multiple resistive contacts among the strands are ameliorated. These characteristics allow the conductor to be a much better conductor of data signals in the very-high and ultra-high frequency ranges.

Figure 4:
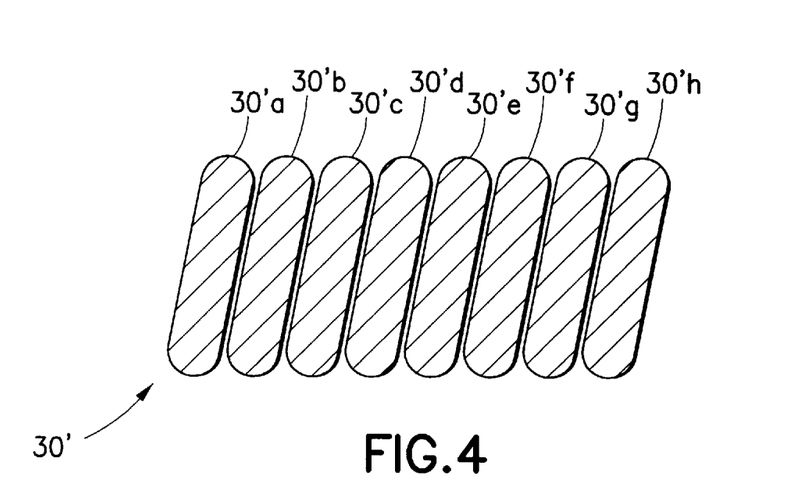
FIG. 4 is a schematic illustration of an electrical coil formed with the conductor of FIG. 3.

Turning now to FIG. 4, as mentioned above, the conductor 30' may be wound into a coil such as that shown in FIG. 4. The exemplary coil shown in FIG. 4 is made from the conductor 30' shown in FIG. 3 and has, for example, eight turns 30'a through 30'h. The turns are imparted into the conductor 30' prior to subjecting the conductor to the heat treatment described above. In practice, the compressed conductor can be wound into a coiled structure such as that shown in FIG. 4 while it is still very flexible, then converted to a more rigid conductor without the losses in efficiency caused by the lay effect and the pinch effect. According to the invention, the multiply-stranded compressed conductor 30' is produced as described above with conductive coatings on at least some of the strands which can be melted after the conductor has been bent into its final shape. If desired, the compressed conductor is insulated with a material which can withstand temporarily being heated to the temperature needed to melt the conductive coating. The conductor is wound or bent into the desired shape and the completed structure is baked to melt the conductive coating. The structure is then cooled to solidify the conductive coating, thereby brazing the multiple-strand conductor and removing some of its flexibility.

According to still another embodiment of the invention, it has been found to be desirable to shape conductors to a non-circular cross section for some applications. In particular, it is desirable when making coils that the wound conductor have a rectangular cross section rather than a circular cross section in order to achieve a high degree of spatial efficiency. Thus, according to the invention, a conductor such as the conductor 30 shown in FIG. 3 is mechanically deformed to produce the conductor 30' which has a cross section similar to that shown in FIG. 5. According to a presently preferred embodiment, the conductor 30" is first formed as the conductor 30', with the stranded wires being drawn to a compacted circular cross section as described above. The compacted conductor 30' is then further shaped to a different cross section either before or after brazing as described above.

Figures 5, 6, 7:
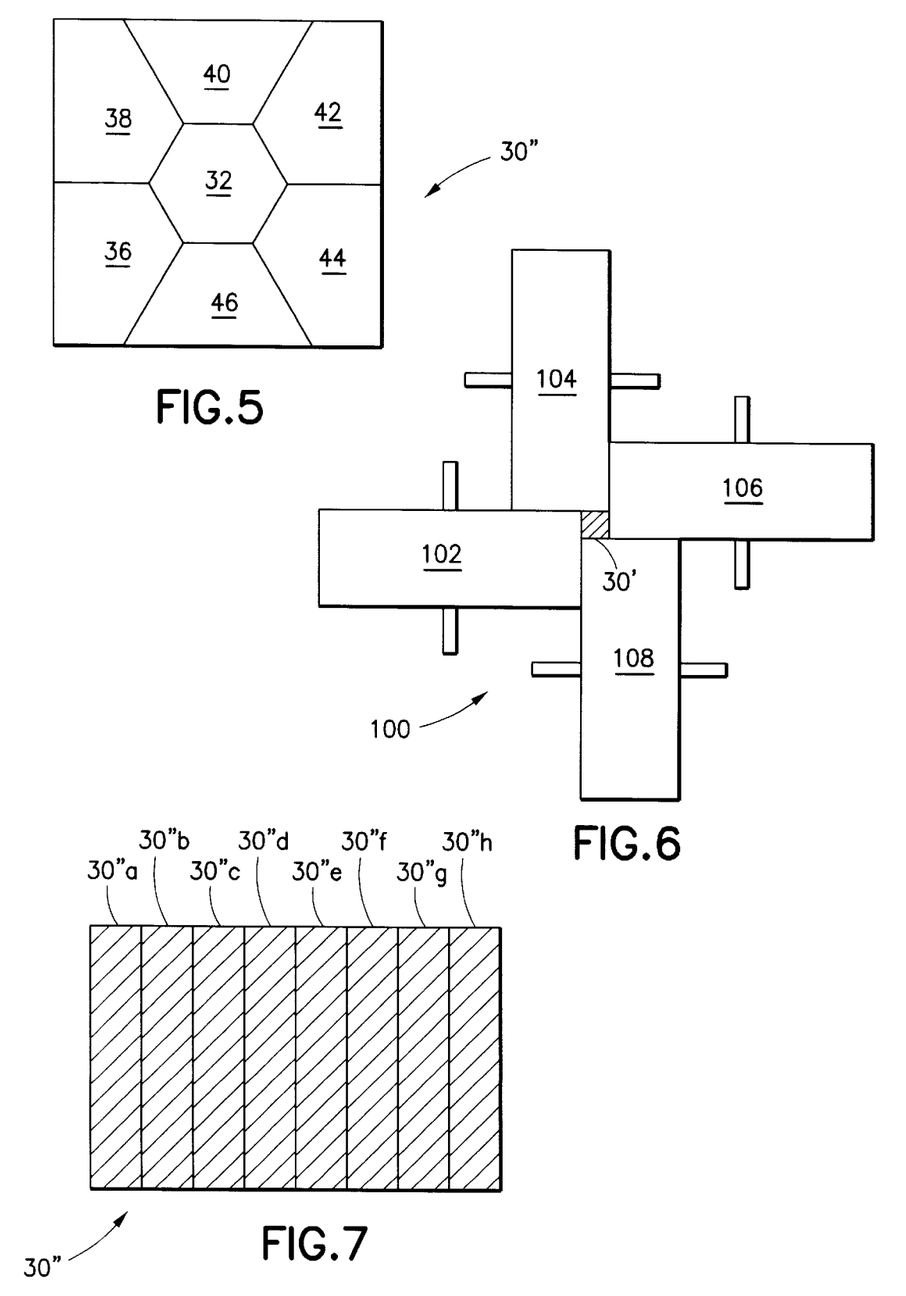
FIG. 5 is a view similar to FIGS. 1–3 of a fourth embodiment of an electrical conductor according to the invention.
FIG. 6 is a schematic illustration of an apparatus used to form the conductor shown in FIG. 5.
FIG. 7 is a schematic illustration of an electrical coil formed with the conductor of FIG. 5.

One manner of deforming the conductor 30' is to use a rolling tool such as that shown schematically in FIG. 6. The tool 100 has four rollers 102, 104, 106, 108 which are arranged in an offset perpendicular manner relative to each other such that a central rectangular space is defined by the surfaces of the rollers. A wire or conductor such as the circular cross section conductor 30' is inserted into the central space defined by the rollers and the rollers are rotated as the wire is fed through the tool 100. Those skilled in the art will appreciate that the dimensions of the rectangular space defined by the rollers is readily altered by relocating the rotational axes of the rollers. According to a preferred embodiment of the invention, the conductor 30' is progressively rolled from its original circular cross section to a rectangular cross section. As with the deformation to the conductor to produce the shape shown in FIG. 3, it is preferable to change the shape of the conductor in gradual steps, e.g., in increments of 10 to 20% until the wire is made substantially rectangular. The degree of compression per step is limited by the amount of compression that can be achieved without causing the multiple strands to become dislodged from each other, reducing the spatial efficiency of the wire, and resulting in unnecessary "pinching" of the wire in subsequent milling steps.

After the initial shape change, the now-rectangular (or square) wire is further reduced in cross-sectional area by further rolling steps. During these subsequent area-reduction steps it is appropriate to reduce the area in steps of approximately 20% per rolling step. It will be appreciated, however, that some metals which are difficult to roll, (such as severely work-hardened materials including cobalt alloys, stainless steels, etc.) need to be reduced by smaller increments. For a given material, once the maximum area reduction (which the material allows) has been achieved (for example, 90% for standard materials such as annealed copper or stainless steel) the wire must be annealed prior to further reduction. In practical operations, since it is easier and less expensive to reduce the area with round wire-drawing dies than with a complex roller arrangement, the wire is preferably first drawn to nearly the desired cross sectional area with round drawing dies, then subjected to the rolling apparatus to produce the square or rectangular shape with a relatively small amount of area reduction, perhaps 20%.

Those skilled in the art will appreciate that other roller arrangements may be used to produce conductors with different shaped cross sections. For example, an hexagonal shaped conductor can be formed with two rollers, each containing a trapezoidal groove. In all cases, however, it is preferable to arrange the rollers such that the wire is not pinched and no "fins" of material are extruded between rollers. If such fins are produced, they must be removed in a subsequent operation.

In all of the methods using multiple rollers, it has been found to be preferable to operate on the entire periphery of the wire at once along its length in order to produce shaped multiple-stranded wire. If, for example, the wire is first rolled between two rollers to flatten it, the strands of the wire may separate, and it may not be practical to then roll the wire with a second set of rollers at ninety degrees to form a square or rectangular wire.

It will also be appreciated that the conductors according to the invention may be shaped to a non-circular cross section by drawing round wire through shaped dies. Such dies are generally produced by combining multiple pieces of hard material (e.g., tungsten carbide or diamond) in the form of wedge-shaped sectors to form a converging die of the desired shape. It is also possible to produce such shaped dies directly by piercing a hard material such as diamond or carbide using methods known in the wire-die making art and including inlet and exit tapers. Since such shaped dies result in reducing the wire in all directions at once, with substantially the entire periphery of the wire confined at a single point on its length, they may be used to produce shaped stranded wire from round, compressed, stranded wire.

Referring now to FIG. 7, the conductor 30" is ideally suited for making a coil such as that shown in FIG. 7 which is compact and spatially efficient. Preferably, the conductor 30" is then wound to form a coil and heated to the eutectic melting point such that the strands are brazed and the cooled coil exhibits a desirable rigidity.

There have been described and illustrated herein several embodiments of an electrical conductor. While particular embodiments of the invention have been described, it is not intended that the invention be limited thereto, as it is intended that the invention be as broad in scope as the art will allow and that the specification be read likewise. Thus, while particular conductive coatings have been disclosed, it will be appreciated that other coatings could be utilized. Similarly, while particular eutectic mixtures have been disclosed, other eutectic mixtures could be utilized. Also, while particular apparatus and methods have been shown for deforming the conductor to assume a circular or non-circular cross section, it will be recognized that other apparatus could be used with similar results obtained. Moreover, while particular configurations have been disclosed in reference to the number of strands in the conductor, it will be appreciated that other configurations could be used as well. For example, conductors according to the invention may be made from three, four, five, seven or more strands around a central core. It will be appreciated that a conductor according to the invention, may include a central core which itself is made from a plurality of strands which are twisted and drawn. It will also be understood that although the examples given herein call for strands with the same diameter, it is possible to utilize aspects of the invention in conductors which are composed of strands having different diameters. For example, the core strand may have a first diameter and all of the outer strands might have a second diameter. Alternatively, the outer strands might vary in size. Furthermore, while the conductors have been disclosed as having particular dimensions, it will be understood that the conductors of many different diameters can be achieved. It will therefore be appreciated by those skilled in the art that yet other modifications could be made to the provided invention without deviating from its spirit and scope as so claimed.

What is claimed is:

1. An electrical conductor, comprising:

a plurality of circular conductive strands twisted around a central conductor to form a bundle, said plurality of circular conductive strands being fused to said central conductor, but not fused to each other, wherein said central conductor includes a first material and said conductive strands include a second material, and said first and second materials together form a eutectic mixture.

2. An electrical conductor according to claim 1, wherein:

said first material is selected from the group consisting of lead, tin, and silver.

3. An electrical conductor according to claim 1, wherein:

after said conductive strands are fused to said central conductor, said bundle is deformed to form a conductive cable having a substantially non-circular cross section.

4. An electrical conductor according to claim 3, wherein:

said conductive cable having a substantially non-circular cross section is wound into a coil.

5. An electrical conductor according to claim 1, wherein: said bundle is wound into a coil.

6. An electrical conductor according to claim 1, wherein:

after said fusing, said bundle is drawn through a die or swaged to form a conductive cable having a substantially circular cross-section.

7. An electrical conductor according to claim 6, wherein:

said conductive cable having a substantially circular cross section is wound into a coil.

8. An electrical conductor according to claim 1, wherein:

said second material is a conductive coating on said conductive strands.

9. An electrical conductor according to claim 8, wherein:

said conductive coating include material selected from the group consisting of lead, tin, and silver.

10. An electrical conductor according to claim 1 wherein:

said central conductor is formed from said first material, and said plurality of conductive strands are coated with said second material.

11. An electrical conductor according to claim 1, wherein:

said second material is a coating on said plurality of conductive strands.

12. An electrical conductor, comprising:

a compacted conductive cable having a substantially circular cross section and having a plurality of conductive strands twisted around a central conductor with each of said plurality of conductive strands being fused to said central conductor, but not fused to each other.

13. An electrical conductor according to claim 12, wherein:

said compacted conductive cable is formed by first taking said conductive strands and twisting said condutive strands around said central conductor to form a bundle, fusing said conductive, strands to said central conductor but not to each other to form a fused bundle, and then either swaing or drawing said fused bundle through a die to compact said conductive cable and provide it with said substantially circular cross section.

14. An electrical conductor according to claim 12, wherein:

wherein said central conductor includes a first material and said conductive strands include a second material, and said first and second materials together form a eutectic mixture.

* * * * *